(12) United States Patent
Tappehorn et al.

(10) Patent No.: US 8,171,811 B2
(45) Date of Patent: May 8, 2012

(54) CONNECTING COMPONENT FOR A BREATHING TUBE WITH A SENSOR FOR MEASURING THE GAS FLOW

(75) Inventors: Ludger Tappehorn, Stockelsdorf (DE); Kirill Koulechov, Timmendorfer Strand (DE); Markus Kratzenstein, Lübeck (DE); Thomas Reinboth, Grosshansdorf (DE)

(73) Assignee: Dräger Medical GmbH, Lübeck (DE)

( * ) Notice: Subject to any disclaimer, the term of this patent is extended or adjusted under 35 U.S.C. 154(b) by 488 days.

(21) Appl. No.: 12/416,374

(22) Filed: Apr. 1, 2009

(65) Prior Publication Data
US 2009/0282896 A1 Nov. 19, 2009

(30) Foreign Application Priority Data
May 17, 2008 (DE) .......................... 10 2008 024 123

(51) Int. Cl.
*G01N 21/00* (2006.01)
(52) U.S. Cl. ...................................... 73/866.5
(58) Field of Classification Search ................. 73/866.5
See application file for complete search history.

(56) References Cited

U.S. PATENT DOCUMENTS

| | | | | |
|---|---|---|---|---|
| 4,304,129 A * | 12/1981 | Kawai et al. | ............... | 73/204.16 |
| 4,709,581 A * | 12/1987 | Nishimura et al. | ............. | 73/202 |
| 4,808,452 A * | 2/1989 | McShane | ........................ | 428/34 |
| 4,911,008 A * | 3/1990 | Casey | ........................... | 73/202.5 |
| 5,060,511 A * | 10/1991 | Sakaue et al. | ............... | 73/204.26 |
| 6,272,933 B1 * | 8/2001 | Gradon et al. | ................. | 73/861 |

FOREIGN PATENT DOCUMENTS

| | | |
|---|---|---|
| CN | 101112637 A | 1/2008 |
| EP | 1 374 940 A2 | 1/2004 |
| GB | 2 272 296 | 6/1994 |
| WO | 2004108218 A1 | 12/2004 |

* cited by examiner

*Primary Examiner* — Hezron E Williams
*Assistant Examiner* — Tamiko Bellamy
(74) *Attorney, Agent, or Firm* — McGlew and Tuttle, P.C.

(57) ABSTRACT

A breathing tube for a sensor (9) with a horizontally extending grip element (11) shall be improved such that the sensor (9) assumes a preferred position in relation to the connecting component (1). To accomplish the object, a wall section (7), which extends flush and at the level of grip element (11), is provided at the connecting component.

13 Claims, 3 Drawing Sheets

CONNECTING COMPONENT FOR A BREATHING TUBE WITH A SENSOR FOR MEASURING THE GAS FLOW

CROSS REFERENCE TO RELATED APPLICATIONS

This application claims the benefit of priority under 35 U.S.C. §119 of German Patent Application DE 10 2008 024 123.7 filed May 17, 2008, the entire contents of which are incorporated herein by reference.

FIELD OF THE INVENTION

The present invention pertains to a connecting component at a breathing tube with a sensor for measuring the gas flow and to a process for centering the sensor at the connecting component.

BACKGROUND OF THE INVENTION

A sensor for measuring the gas flow and the gas temperature in a breathing tube is known from GB 2 272 296 A. The sensor has a T-shaped sensor housing with a horizontally arranged grip element, a conical sensor connection extending at right angles thereto, and temperature-measuring elements at the free end of the sensor connection. The corresponding connecting component for the sensor has a conical mounting sleeve, into which the sensor connection is inserted. The sensor connection is held by static friction within the mounting sleeve.

Sensors for measuring the gas flow of breathing gas have been known to have the sensor connection, at which the temperature-measuring elements are arranged, attached to the connecting component with a preferred direction. Mounting with the preferred direction may be necessary when the direction of the gas flow is also to be determined in addition to the level thereof.

It is also known that a protruding, triangular projection, which meshes with a corresponding depression at the mounting sleeve for the sensor connection, can be arranged at the sensor connection for centering a sensor in relation to a connecting component. Such an arrangement appears from EP 1 374 940 A2. The prior-art centering correspondingly requires design measures on both the sensor and the mounting sleeve of the connecting component.

SUMMARY OF THE INVENTION

An object of the present invention is to improve a connecting component of the type mentioned above such that a sensor for measuring the gas flow can be inserted into the corresponding mounting sleeve at the connecting component in a preferred direction in a simple manner and to propose a method for centering a sensor in relation to the connecting component at the breathing tube.

According to the invention, a combination of a connecting component at a breathing tube and a sensor is provided for measuring the gas flow in the breathing tube. The sensor has a T-shaped sensor housing with a horizontally arranged grip element, with a conical sensor connection extending at right angles thereto and temperature-measuring elements at the free end of the sensor connection. The connecting component has a conical mounting sleeve for the sensor connection and a wall section, which extends flush with the grip element at least partly and extends into the area of grip element.

According to another aspect of the invention, a connecting component is provided at a breathing tube for a sensor with a horizontally extending grip element for measuring the gas pressure in the breathing tube. The connecting component has a conical mounting sleeve for a sensor connection of sensor. The sensor connection is designed correspondingly thereto. A wall section extends flush with the grip element, at least partly, and extends into the area of the grip element.

According to still another aspect of the invention, a method is provided for centering a sensor with a horizontally extending grip element for measuring the gas flow in a breathing tube in relation to a connecting component. A wall section is provided, which extends flush with the grip element at least partly and extends up to the grip element. The wall section is provided at the connecting component in the area of a mounting sleeve for a sensor connection of a sensor.

The advantage of the present invention is that the grip element and hence the temperature-measuring elements of the sensor can be aligned in relation to the connecting component due to a wall section, which extends flush with the grip element, is arranged at the connecting component in the vicinity of the mounting sleeve and extends at the level of the grip element. The T-shaped sensor housing can be used at the same time by means of the wall section to center the temperature-measuring elements within the gas channel.

The wall section is defined as a projection, which extends at least partly towards the preferred position of the grip element, is arranged at the connecting component, extends up into the area of the grip element and prevents the grip element from rotating in relation to the connecting component. The preferred position of the grip element and hence the preferred position of the temperature-measuring elements connected to the grip element are set by positioning the projection at the connecting component. As an alternative to a projection, it is also possible to use centering pins, which fix the grip element in the preferred position. The projection or centering pins may also be arranged on both sides of the grip element. The projection or centering pins must be designed in terms of height such that they touch the grip element on the side and prevent twisting at least when the sensor connection is inserted into the mounting sleeve.

The outer contour of the sensor connection and the inner contour of the mounting sleeve, which inner contour is designed correspondingly, are standardized in sensors for measuring the gas flow in breathing tubes, so that a plurality of sensors can be used. To adapt the wall section or centering pins to different grip elements of the sensors, the wall section may be manufactured from an elastic material, so that it can adapt itself to the particular diameter of the grip element by elastic deformation. Prior-art sensors for measuring the gas flow often have a T-shaped sensor housing, in which the connecting cable is led away on the side to prevent damage. The centering described according to the present invention can thus be used for a plurality of commercially available sensors.

The method for centering a sensor for measuring the gas flow, which has a horizontally extending grip element, in relation to a connecting component comprises the arrangement of a wall section, which extends flush with the grip element and extends up to the level of the grip element at the connecting component in the area of a mounting sleeve for a sensor connection of the sensor.

An exemplary embodiment of the present is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
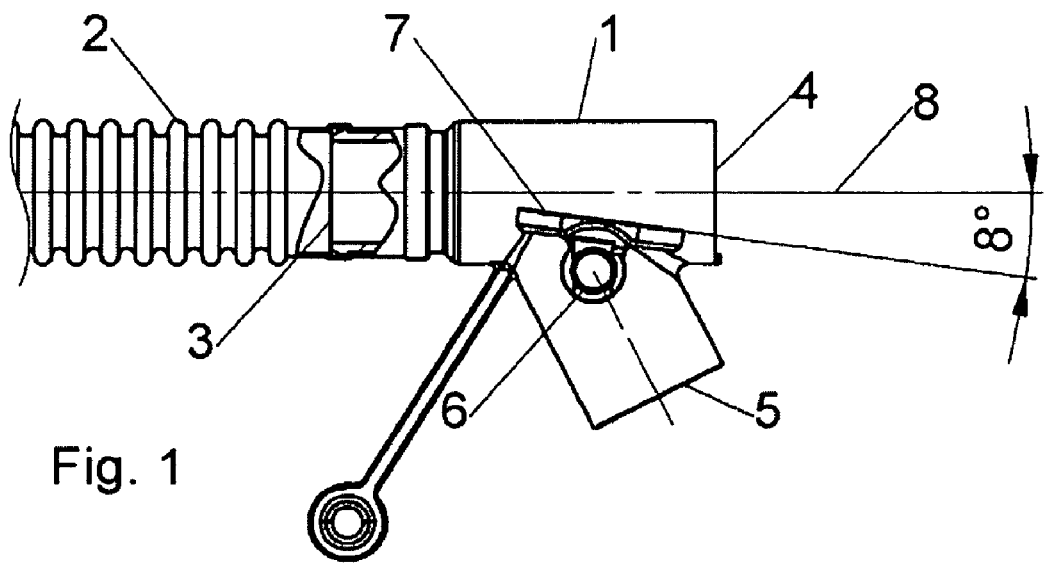
FIG. 1 is a side view of a connecting component.

Referring to the drawings in particular, FIG. 1 illustrates in a perspective view a connecting component 1 at a breathing tube 2, of which only a section is shown. Connecting component 1 has three connecting sockets 3, 4, 5, which are in flow connection with one another within the connecting component 1. A conically shaped mounting sleeve 6 is arranged at the connecting component 1 for attaching a sensor, which is not shown in more detail. A wall section 7 arranged in the vicinity of the mounting sleeve extends at an acute angle of approximately 8° relative to a longitudinal axis 8 of connecting component 1.

Figure 2:
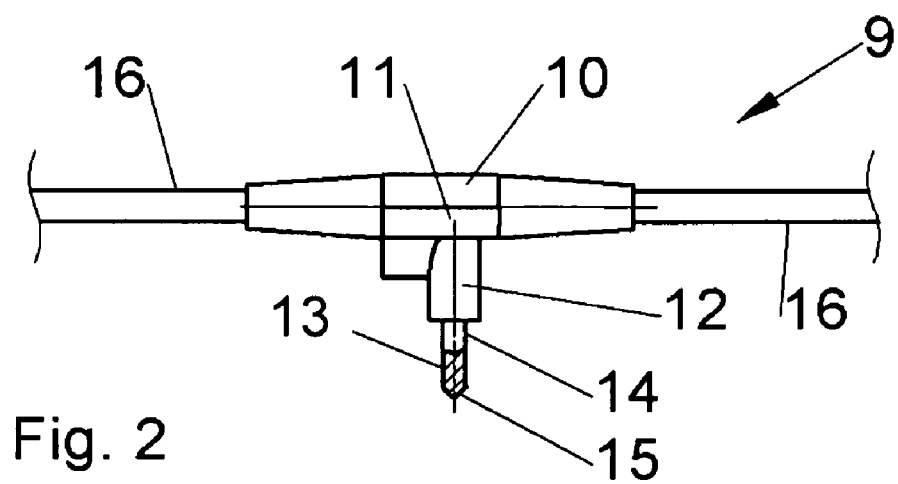
FIG. 2 is a side view of a sensor.

FIG. 2 shows the side view of a sensor 9. A sensor housing 10 of sensor 9 comprises a horizontally extending grip element 11 with a sensor connection 12, which exits from it downwardly and is of a conical shape. A bracket 13 with temperature-measuring elements 14, 15 is located at the free end of the sensor connection 12. The sensor connection 12 has a shape corresponding to the mounting sleeve 6 of the connecting component 1, and firm and gas-tight seating of the sensor housing 10 in the connecting component 1 is achieved by the conical surface contour.

Figure 3:
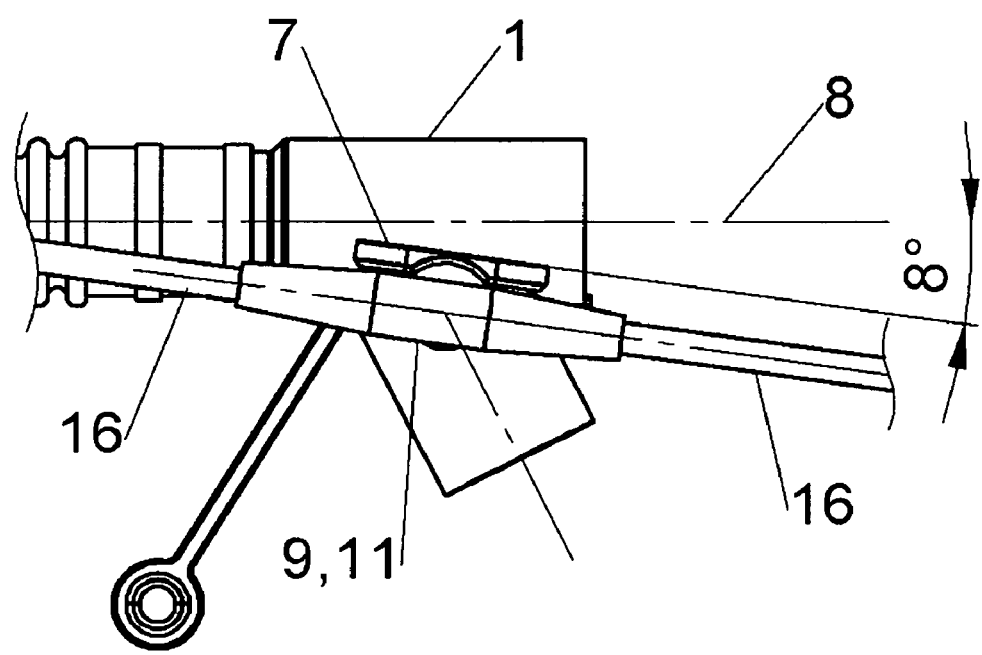
FIG. 3 is a side view of the connecting component with the sensor inserted.

FIG. 3 shows the connecting component 1 with the sensor 9 inserted. The height of wall section 7 is dimensioned such that it extends in the area of the grip element 11 and secures same against twisting.

Figure 4:
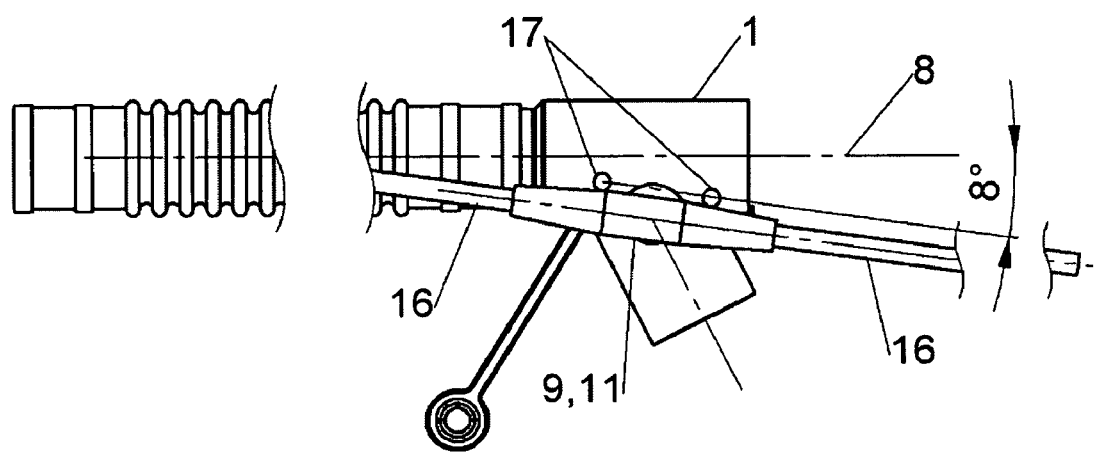
FIG. 4 is a side view showing an alternative embodiment to FIG. 3.

FIG. 4 illustrates an alternative connecting component 1, in which the wall section 7 is replaced by two centering pins 17 compared to FIG. 3. A connection line between the centering pins 17 extends flush with grip element 11.

While specific embodiments of the invention have been shown and described in detail to illustrate the application of the principles of the invention, it will be understood that the invention may be embodied otherwise without departing from such principles.

APPENDIX

List of Reference Numbers

1 Connecting component
2 Breathing tube
3, 4, 5 Connecting sockets
6 Mounting sleeve
7 Wall section
8 Longitudinal axis
9 Sensor
10 Sensor housing
11 Grip element
12 Sensor connection
13 Holder
14, 15 Temperature-measuring element
16 Connection cable
17 Centering pin

What is claimed is:

1. A breathing tube and a connecting component combination comprising:
a breathing tube;
a sensor for measuring a gas flow in the breathing tube, said sensor having a T-shaped sensor housing with a horizontally arranged grip element having a sensor connection extending at right angles thereto and temperature-measuring elements at a free end of said sensor connection; and
a connecting component having a mounting sleeve for receiving said sensor connection and having a wall section extending away from said mounting sleeve, said wall section being arranged flush or partly flush with the grip element and extending at least partially into an area of said grip element spaced from said mounting sleeve.

2. A connecting component for a sensor, the connecting component being provided at a breathing tube for the sensor, the sensor having a horizontally extending grip element for measuring gas pressure in the breathing tube, the connecting component comprising:
a mounting sleeve for receiving a sensor connection of the sensor, which said sensor connection is designed correspondingly thereto; and
a wall section extending away from said mounting sleeve, said wall section being arranged flush with the grip element and at least partly and extends into an area the grip element spaced from said mounting sleeve.

3. A method for centering a sensor, the method comprising:
providing a breathing tube;
providing a sensor for measuring a gas flow in the breathing tube, said sensor having a T-shaped sensor housing with a horizontally arranged grip element having a sensor connection extending at right angles thereto and temperature-measuring elements at a free end of said sensor connection;
providing a connecting component having a mounting sleeve for receiving said sensor is connection and having a wall section extending outwardly from said mounting sleeve; and
connecting the sensor connection to the mounting sleeve and positioning the grip element flush with the wall section, with the wall section extending at least partly up to the grip element to an area spaced from said mounting sleeve.

4. A connecting component combination in accordance with claim 1, wherein:
said mounting sleeve and said sensor connection are shaped to have said sensor connection fit into said mounting sleeve in a plurality of rotational positions, each of said rotational positions forming a gas tight seal between said mounting sleeve and said sensor connection.

5. A connecting component combination in accordance with claim 1, wherein:
said wall section and said grip element are shaped and arranged to create a physical interference which blocks rotation of said sensor connection in said mounting sleeve, said physical interference being spaced from said mounting sleeve and said sensor connection.

6. A connecting component in accordance with claim 2, wherein:

said wall section and said grip element are shaped and arranged to create a physical interference which blocks rotation of said sensor connection in said mounting sleeve, said physical interference being spaced from said mounting sleeve and said sensor connection.

7. A connecting component in accordance with claim 6, wherein:
said mounting sleeve and said sensor connection are shaped to have said sensor connection fit into said mounting sleeve in a plurality of rotational positions, each of said rotational positions forming a gas tight seal between said mounting sleeve and said sensor connection.

8. A connecting component in accordance with claim 7, wherein:
said sensor is a directional sensor.

9. A method in accordance with claim 3, wherein:
said wall section and said grip element are shaped and arranged to create a physical interference which blocks rotation of said sensor connection in said mounting sleeve, said physical interference being spaced from said mounting sleeve and said sensor connection.

10. A method in accordance with claim 3, wherein:
said sensor is a directional sensor.

11. A connector arrangement measuring a parameter in a breathing tube, the connector arrangement comprising:
a T-shaped sensor housing having a grip element forming a top of said T-shaped housing, and having a sensor connection extending at right angles to said grip element and forming a leg of said T-shaped housing;
a sensor arranged at a free end of said sensor connection, said sensor measuring the parameter in the breathing tube;
a connecting component adapted to connect to the breathing tube, said connecting component defining a mounting sleeve adapted to receive said sensor connection, said mounting sleeve and said sensor connection being shaped to have said sensor connection able to fit into said mounting sleeve in a plurality of rotational positions, each of said rotational positions forming a gas tight seal between said mounting sleeve and said sensor connection, said connecting component having a wall section extending outwards from said mounting sleeve, said wall section and said grip element being shaped and arranged to limit said plurality of rotational positions of said sensor connection in said mounting sleeve when said sensor connection is arranged in said mounting sleeve.

12. A connector arrangement in accordance with claim 11, wherein:
said wall section and said grip element are shaped and arranged to create a physical interference which blocks rotation of said sensor connection in said mounting sleeve, said physical interference being spaced from said mounting sleeve and said sensor connection.

13. A connector arrangement in accordance with claim 11, wherein:
said sensor is a directional sensor.

\* \* \* \* \*